US012673079B2

(12) United States Patent

Arpini et al.

(10) Patent No.: US 12,673,079 B2

(45) Date of Patent: Jul. 7, 2026

(54) COMPOSITIONS COMPRISING AN AMERICAN CRANBERRY EXTRACT AND PHOSPHOLIPIDS

(71) Applicant: Indena S.P.A., Milan (IT)

(72) Inventors: Sabrina Arpini, Milan (IT); Giacomo Mombelli, Milan (IT); Paolo Morazzoni, Milan (IT); Federico Peterlongo, Milan (IT); Antonella Riva, Milan (IT); Massimo Ronchi, Milan (IT)

(73) Assignee: Indena S.P.A., Milan (IT)

( * ) Notice: Subject to any disclaimer, the term of this patent is extended or adjusted under 35 U.S.C. 154(b) by 0 days.

(21) Appl. No.: 18/674,967

(22) Filed: May 27, 2024

(65) Prior Publication Data

US 2024/0390442 A1 Nov. 28, 2024

Related U.S. Application Data

(62) Division of application No. 17/262,148, filed as application No. PCT/IB2019/056261 on Jul. 23, 2019, now abandoned.

(30) Foreign Application Priority Data

Jul. 23, 2018 (IT) ........................ 102018000007440

(51) Int. Cl.

| | |
|---|---|
| *A61K 36/45* | (2006.01) |
| *A61K 31/685* | (2006.01) |
| *A61P 13/02* | (2006.01) |
| *A61P 31/00* | (2006.01) |

(52) U.S. Cl.

CPC ............ *A61K 36/45* (2013.01); *A61K 31/685* (2013.01); *A61P 13/02* (2018.01); *A61P 31/00* (2018.01); *A61K 2236/51* (2013.01)

(58) Field of Classification Search

None

See application file for complete search history.

(56) References Cited

U.S. PATENT DOCUMENTS

| | | | | |
|---|---|---|---|---|
| 5,043,323 A | * | 8/1991 | Bombardelli | .......... A61K 8/553 514/844 |
| 8,084,067 B2 | | 12/2011 | Giori et al. | |
| 8,652,492 B2 | | 2/2014 | Sun et al. | |
| 8,652,494 B2 | | 2/2014 | Rebmann | |

FOREIGN PATENT DOCUMENTS

| | | |
|---|---|---|
| IT | MI20070444 A1 | 9/2008 |
| WO | 2010150051 A1 | 12/2010 |

OTHER PUBLICATIONS

Choudhury A., et al., "Phytosome: A novel dosage form for herbal drug delivery", Journal of Applied Pharmaceutical Research, 2014, 2(2), 44-52 [1].

Gnananath K., et al., "Phospholipid Complex Technique for Superior Bioavailability of Phytoconstituents", Advanced Pharmaceutical Bulletin, 2017, 7(1), 35-42.

Office Action issued Jun. 11, 2024 from Australian patent office in connection to counterpart application No. 2019311840.

"Is the Effect of cranberry soft capsules good?", Ask a Doctor Online and Get all Questions Answered https://www.120ask.com/question/48874894.htm, p. 1, Dec. 10, 2013.

Amin et al. (2012) Inern J. Advancement of R&D, vol. 1, issue 3: 1-15 (2012).

Bombardelli et al., (1991) Cosmetics and toiletries, vol. 106, No. 3, 69-73.

Choubey et al. (2017) IJPSR vol. 2(4): 807-815.

English Translation of Office Action of Nov. 3, 2021Issued in counterpart Chinese Application No. 201980049079.8.

Gnananath et al., 2017, adv Parm. Bull. 7(1): 35-42.

Hong et al., "Phospholipid Chemistry and Application Technology", China Metrology Press, May 31, 2006, pp. 150-151.

Huffnagle et al., "The probiotics Revolution", NanHai Publishing Co., Oct. 31, 2009.

Kadu A S. et al., "Phytosome: a novel approach to enhance the bioavailability of phytoconstituent", Asia J. Pharmaceutics, 11(2): 5453-5456 (2017).

Ledda A et al., "Supplementation with high titer cranberry extract (Anthocran) for the prevention of recurrent urinary tract infections in elderly men suffering from moderate prostatic hyperplasia: a pilot study", European Review for Medical and Pharmacological Sciences, vol. 20, No. 24, Nov. 30, 2016, pp. 5205-5209.

Ledda A. et al., "Meriva, a lecithinized cur cumin delivery system, in the control of benign prostatic hyperplasia: a pilot, product evaluation registry study", Panminerva Medica, vol. 54, No. 1. supplementation. 4, Nov. 30, 2012, pp. 17-22.

Leddda et al, 2016 Eur. Rev.Med. Pharmacol. Sci. 20:5205-5209.

Letter reporting office action issued Nov. 3, 2021 in chinese counterpart application No. 201980049079.8.

Nett C. C., "Cranberry and blueberry: evidence of protective effects against cancer and vascular diseases", Mol. Nutr Res 2007, 51, 652-664.

Pawar H A et al., "Phytosome as a novel biomedicine: a microencapsulated drug delivery system", Journal of Bioanalysis & Biomedicine, 2015 7:1, 0006-012.

Riva A et al., "Improved oral absorption of quercetin from querceting phytosome(R) , a new delivery system based on food grade lecithin", Eur. J. Drug. Metabol. Pharmacokinetics 44: 169-177 (2019).

(Continued)

*Primary Examiner* — Russell G Fiebig

(74) *Attorney, Agent, or Firm* — Silvia Salvadori, P.C.; Silvia Salvadori

(57) ABSTRACT

The present invention relates to compositions comprising an American cranberry extract combined with phospholipids, and the use thereof in the prevention and treatment of urinary tract infections. The invention also relates to processes for the preparation of said compositions, and formulations for oral administration comprising said compositions.

3 Claims, 2 Drawing Sheets

(56)         References Cited

OTHER PUBLICATIONS

Search Report and Written Opinion of PCT/IB2019/056261 of Sep. 30, 2019.
Singh A P et al., "Isolation of specific cranberrry flavonoids for biological activity assessment", Food Chemistry, 116, 963-968 (2009).
Van Nieuwenhuyzen W et al. "Update on vegetable lecithin and phospholipid technologies", Eur. J. Lipic Sci. Technol. 2008, 110, 472-486.

* cited by examiner

COMPOSITIONS COMPRISING AN AMERICAN CRANBERRY EXTRACT AND PHOSPHOLIPIDS

The invention relates to pharmaceutical or nutraceutical compositions comprising plant extracts, and in particular to compositions useful in the treatment and prevention of bacterial infections of the urinary tract.

PRIOR ART

The juice and extracts of American cranberry (*Vaccinium macrocarpon* Aiton) have formed the subject of numerous clinical trials for the treatment and prevention of lower urinary tract infections (Burleigh A. E. et al. *Nutr J* 2013; 12:139, Ledda A. et al. *Eur Rev Med Pharmacol Sci* 2017; 21:389-393, Jepson R G. et al. *Cochrane Database Syst Rev* 2012; 10: CD001321). Recurrent infections of the lower urinary tract affect about 50% of adult women (Wang A. et al. *Prim Care* 2013; 40:687-706), and can also affect men, though with a lower frequency. In men, the incidence of lower urinary tract infections increases significantly with age, because of the structural and functional alteration that the urinary tract undergoes as a result of aging. Said alteration is usually manifested as the condition known as benign prostatic hyperplasia (Schaeffer A J. et al. *N Engl J Med* 2016; 374:562-571).

The main pathogen of lower urinary tract infections is the bacterium *Escherichia coli*, followed by *Proteus* spp., *Staphylococcus saprophyticus, Klebsiella* spp. and other Enterobacteriaceae (Kahlmeter G. J. *Antimicrob Chemother* 2000; 46:15-22).

Lower urinary tract infections are classed as recurrent if at least three episodes occur in a year, or two episodes in six months. The frequency of said episodes can be reduced by antibiotic prophylaxis, but long-term antibiotic treatments increase health costs and can generate resistance to the efficacy of antimicrobial treatments, and alterations of the intestinal bacterial flora.

The identification of non-antibiotic treatments able to prevent the onset of recurrent lower urinary tract infections would therefore be of great interest.

The possible non-antibiotic treatments include diet supplements containing American cranberry extracts, which have been given a great deal of attention. The American cranberry contains numerous organic substances, including proanthocyanidins (PACs), flavonols, polyphenols and hydroxycinnamic acids which, together with their active metabolites, possess both direct and indirect bactericidal activity. The latter is due to their ability to prevent adherence to the urothelial mucosa, thereby preventing the formation of biofilms by said pathogens. Said antiadhesion activity has been demonstrated, in particular, for proanthocyanidins, the main active constituents of American cranberry. In vitro and in vivo tests have demonstrated that proanthocyanidins inhibit the adherence of the P fimbriae of *Escherichia coli* to the urothelial mucosa of the urinary tract (Howell A B. et al. *N Engl J Med* 1998; 339:1085-1086, Di Martino P. et al. *J Urol* 2006; 24:21-27).

The antibacterial activity of some of the main metabolites of the active constituents present in American cranberry extracts, such as protocatechuic acid and gallic acid, on the strains responsible for lower urinary tract infections, is described, for example, by Kakkar, Sahil et al., *ISRN pharmacology* 2014 (2014), Miklasińska, Maria, et al. *Molecules* 20.8 (2015): 13536-13549 and Jayaraman, Premkumar, et al.

*International journal of biological sciences* 6.6 (2010): 556-Mensah, J. K. et al., *Current Science Perspectives* 1.2 (2015): 69-76).

However, the efficacy data obtained to date for American cranberry derivatives in the treatment and prevention of urinary tract infections are somewhat variable. This is due partly to the use of extracts which are neither well characterised nor reproducible, and have an excessively low active ingredient content, and above all to the use of unsuitable compositions and formulations, which are unable to promote the absorption of the active ingredients following oral administration, and above all do not allow the active metabolites to reach effective concentrations in the urine.

The availability of compositions able to promote the absorption of the active constituents of American cranberry and the metabolites thereof following oral administration, and to ensure that effective concentrations are reached in the urine, could therefore represent an important tool, which is alternative or complementary to antibiotic treatment, in the treatment and prevention of urinary tract infections.

Compositions obtained from a combination of botanical extracts with natural or synthetic phospholipids are described, for example, in EP 0209037 (IdB Holding S.p.A.), EP 0275005 (Indena S.p.A.), EP 0283713 (Indena S.p.A.) and WO 2007/118631 (Indena S.p.A.).

WO2010/150051 (Lipoid GmbH) describes compositions containing an active plant ingredient or a plant extract, a sugar, preferably a maltodextrin, and phospholipids. Said compositions are obtained by dissolving or dispersing the ingredients simultaneously or successively at room temperature in water. This step is followed by a process of homogenisation, filtration and drying, and optionally grinding to the desired particle size. In particular, WO2010/150051 claims an active plant ingredient content ranging between 0.5% and 40% by weight, a maltodextrin content ranging between 10% and 90% by weight, and a phospholipid content ranging between 0.5% and 30% by weight. Said document states that the compositions are characterised by high stability during transport and storage, and ease of incorporation in various dosage forms for the pharmaceutical, nutrition and cosmetic industries. It also states that the compositions are characterised by good solubility and wettability, which guarantee high bioavailability of the active plant ingredient. The active plant ingredients cited in WO2010/150051 include American cranberry extract (*Vaccinium macrocarpon*). However, no composition containing American cranberry extracts is specifically described. Moreover, no in-vivo data are cited to demonstrate the actual increase in the bioavailability of the active ingredients contained in the compositions, and in particular that effective concentrations of the active metabolites are reached in the excreted urine after oral administration, a condition that represents a pre-requisite for a curative and preventive action towards urinary infections.

There is consequently still a need to provide compositions based on American cranberry which guarantee measurable, effective levels of the active ingredients, and in particular of their metabolites, in the urine.

SUMMARY OF THE INVENTION

The present invention relates to a composition, typically in solid form, comprising:
- a) a *Vaccinium macrocarpon* extract in amounts ranging from 20% to 50% by weight of the total weight of the composition, and b) at least one phospholipid in amounts ranging from 50% to 80% by weight of the total weight of the composition.

The invention also relates to a process for the preparation of said composition and pharmaceutical or nutraceutical formulations for oral administration comprising said composition. The invention also relates to the compositions as described above, and to the corresponding formulations for use in the treatment and prevention of urinary tract infections.

DETAILED DESCRIPTION OF THE INVENTION

Figure 1:
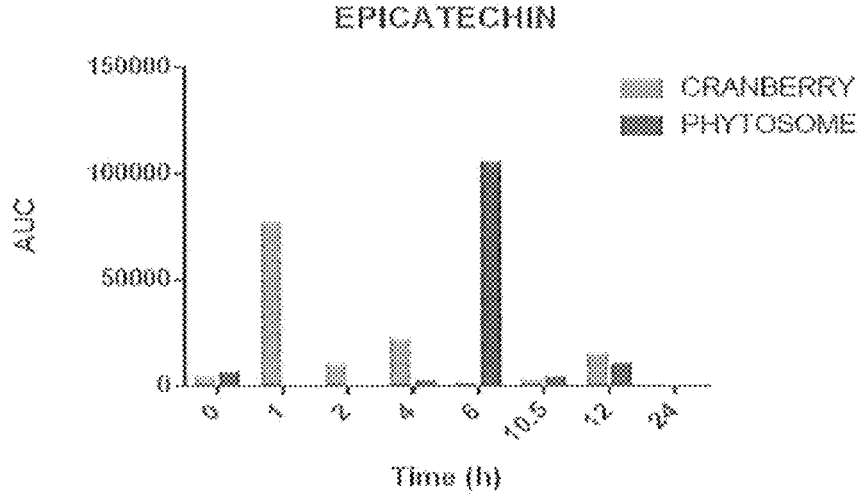
FIG. 1 shows the area under the curve of epicatechin.
Figure 2:
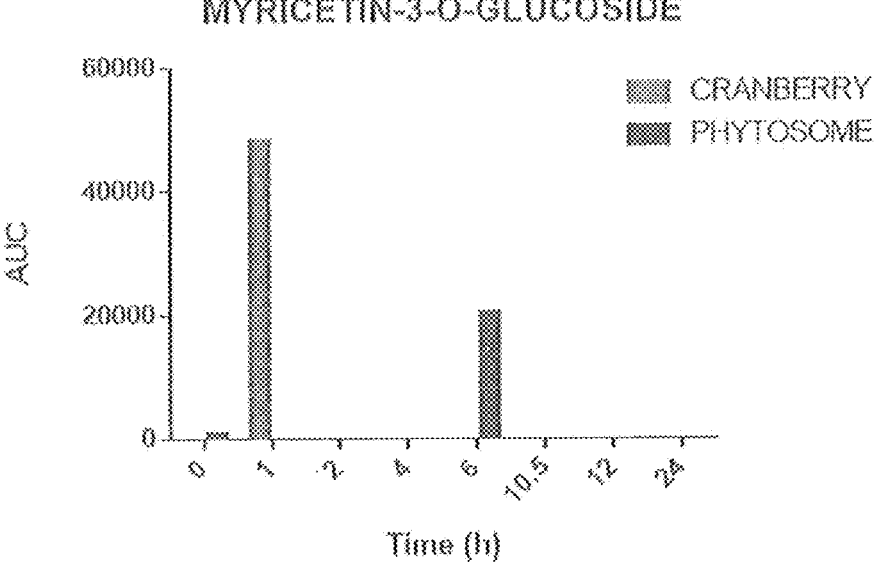
FIG. 2 shows the area under the curve of myricetin-3-O-glucoside.
Figure 3:
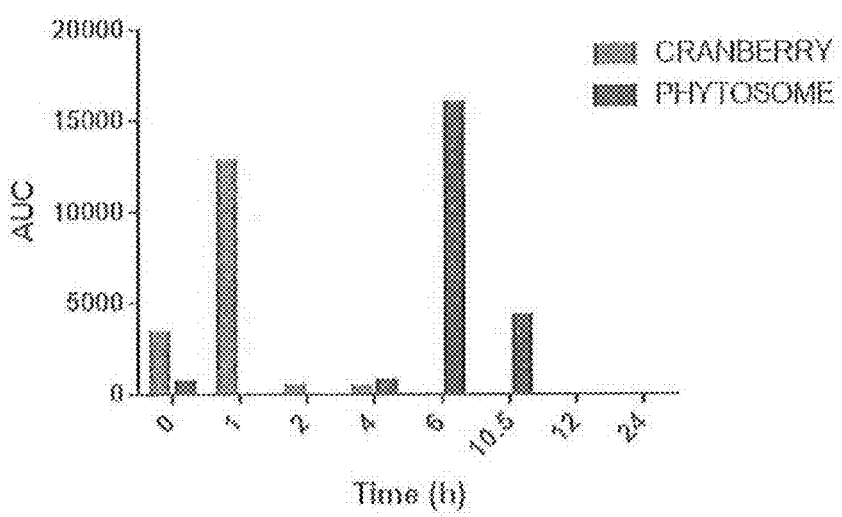
FIG. 3 shows the area under the curve of myricetin-3-β-O-galactoside.

It has surprisingly been found that by combining an American cranberry (*Vaccinium myrtillus*) extract, preferably an extract characterised by a high proanthocyanidin (PAC) content, with a high percentage of a phospholipid (PL), in particular by means of the preparation process described below, measurable, effective urinary concentrations of the active metabolites of the active ingredients contained in the extract can be reached in vivo. In particular it has been found that the compositions according to the invention can be administered in smaller amounts than an American cranberry extract having the same proanthocyanidin content but not in combination with phospholipids, while still guaranteeing that effective concentrations are reached in the urine, and therefore in contact with the urothelial mucosa.

It has also surprisingly been found that after administration of the formulations according to the invention, the main metabolites appear in the urine at different times, in particular at later times than those observed after the administration of control formulations containing an extract "as is", i.e. without phospholipid. The invention therefore also relates to formulations containing an American cranberry extract combined with phospholipids and an American cranberry extract "as is", i.e. not combined with phospholipids.

The compositions according to the invention contain:
a) 20% to 50% (w/w) of an American cranberry extract, preferably characterised by a proanthocyanidin content ranging between 15 and 40% (w/w);
b) 50% to 80% (w/w) of a phospholipid or a mixture of phospholipids.

The compositions according to the invention can optionally contain 1% to 30% by weight, relative to the total weight of the composition, of one or more technological adjuvants such as diluents, glidants or lubricants which improve the physical characteristics of the compositions and facilitate their incorporation in the formulations.

In a preferred aspect, the compositions consist of an American cranberry extract and a phospholipid or mixture of phospholipids in the amounts specified above, corresponding to a weight ratio between extract and phospholipid ranging between 1:1 and 1:4. In another preferred aspect, the compositions consist of an American cranberry extract, a phospholipid or mixture of phospholipids, and one or more adjuvants, in the amounts specified above. The American cranberry extract and the phospholipids, in the ratios and under the conditions reported, can take the form of a molecular complex following interactions between the chemical functions of the ingredients of the extract and those of the phospholipids.

For the purposes of the invention, the expression "American cranberry extract" identifies an extract obtainable by a process of organic extraction from *Vaccinium macrocarpon* berries and, preferably, from the juice obtained by crushing them. The extract can subsequently be concentrated to increase the content of proanthocyanidins, which are considered to be the main, though not the only, active ingredients of the biomass. The extract preferably has a proanthocyanidin content ranging between 15% and 40% (w/w), more preferably between 25% and 35% (w/w), measured by the DMAC (4-dimethylaminocinnamaldehyde) colorimetric method (R. L. Prior et al., J Sci Food Agric 2010; 90; 1473-1478).

A preferred example of a cranberry extract with a high proanthocyanidin content is commercially available from Indena S.p.A. as Anthocran™.

For the purposes of the present invention, the term "phospholipid" identifies lecithins obtainable from soy bean, sunflower or another plant or animal source, preferably a plant source, and preferably lecithins selected from phosphatidylcholine, phosphatidylserine and phosphatidylethanolamine, having the same or different acyl groups, mainly palmitic, stearic, oleic, linoleic and linolenic acid derivatives. The term "mixture" referring to phospholipids identifies a mixture of lecithins originating from the same plant source or from different plant sources. The expression "at least one phospholipid" identifies a single phospholipid or a mixture of phospholipids.

Adjuvants which can be contained in the compositions according to the invention are typically selected from one or more:
diluents which are water-soluble or water-insoluble at room temperature, such as for example microcrystalline cellulose, calcium phosphate, calcium carbonate, mannitol, maltodextrins, isomalt or combinations thereof;
lubricants and/or glidants, such as silicon dioxide, talc, stearic acid, magnesium stearate or combinations thereof;
surfactants, such as sucrose esters, polysorbates, polyoxyethylene castor oil derivatives, D-α-tocopheryl-polyethylene glycol succinate (vitamin E TPGS) or combinations thereof.

These and further excipients are described in Remington: "The Science and Practice of Pharmacy", 22nd edition, Pharmaceutical Press, 2013.

In a preferred aspect, the compositions do not contain sugars, and in particular do not contain maltodextrins, mannitol, isomalt or combinations thereof.

In a second aspect, the invention relates to a process for obtaining the compositions and to the compositions obtainable by said process.

In particular, the process comprises solubilisation or dispersion of an American cranberry extract and at least one phospholipid, and optionally at least one adjuvant, in an organic solvent suitable for pharmaceutical and/or nutraceutical use, preferably selected from ethyl alcohol, ethyl acetate and acetone, at a temperature ranging between 30° C. and 90° C., preferably between 50° C. and 90° C., to obtain a solution or dispersion from which the organic solvent is subsequently removed to obtain the solid composition according to the invention.

In a preferred aspect thereof, the process comprises simultaneous solubilisation or dispersion of an American cranberry extract and at least one phospholipid in an organic solvent, followed by optional addition of one or more adjuvants. According to said aspect, the process comprises the following steps:

a-1) solubilising or dispersing the extract and the phospholipid in 10-20 volumes of an organic solvent, preferably selected from ethyl alcohol, ethyl acetate and acetone, until a solution or a homogeneous dispersion is obtained;

b-1) heating the solution/dispersion obtained in step a) at a temperature ranging between 30° C. and 90° C., preferably between 50° C. and 90° C., typically maintaining the system under stirring until a solution or a homogeneous dispersion is obtained. Heating is necessary to maximise the solubility of the extract and the phospholipid;

c-1) optionally adding one or more adjuvants to the solution or dispersion in step b-1), maintaining stirring under the same temperature conditions as in step b), until a solution or a homogeneous dispersion is obtained;

d-1) removing the solvent, preferably by evaporation at low pressure, more preferably between 10 and 60 MPA, from the solution or dispersion obtained in step b) or c), maintaining a temperature preferably ranging between 50° C. and 70° C., more preferably 70° C., optionally completing the solvent removal by drying under vacuum in a stove set to a temperature ranging between 50° C. and 90° C., until a solid composition is obtained which typically has a solvent residue falling below the limits specified in ICH Guideline Q3C (R6) relating to residual solvents;

e-1) calibrating the solid composition obtained at the end of step d) on an 0.25 to 2.0 mm mesh screen, and optionally adding a lubricant and/or a glidant, preferably selected from stearic acid, magnesium stearate and silicon dioxide, preferably silicon dioxide.

In another preferred aspect thereof, the process involves the solubilisation or dispersion of the extract in the solvent until a solution or dispersion is obtained, and adding at least one phospholipid, and optionally one or more adjuvants, to said solution or dispersion. In particular, according to said aspect, the process comprises:

a-2) solubilising or dispersing the American cranberry extract or phospholipid in the organic solvent until a homogeneous solution or dispersion is obtained;

b-2) adding the American cranberry extract or phospholipid to the resulting solution or dispersion, heating and maintaining the mixture under stirring under the experimental conditions described in paragraph b);

proceeding with steps c-1), d-1) and e-1) as described above, until the process is complete.

For the avoidance of doubt, for the purposes of the present invention, the term "solution" indicates a liquid composition which appears clear on visual inspection; the term "dispersion" indicates a liquid composition which, on visual inspection, contains suspended particles and appears opaque and cloudy, but still homogeneous.

Moreover:

where numerical ranges are specified in the present description and claims, the extremes of the ranges shall be deemed to be included;

the term "process" is synonymous with "method";

the expressions "at least one" and "one or more of" are equivalent, and can be used interchangeably;

In a third aspect thereof, the invention relates to solid formulations for oral administration which comprise a composition according to the invention mixed with one or more pharmaceutically or nutraceutically acceptable excipients. Examples of formulations comprise granulates, tablets and capsules, optionally suitable for modified release, which the skilled person can prepare by known methods and with known excipients, such as those described in Remington: *"The Science and Practice of Pharmacy"*, 22nd edition, Pharmaceutical Press, 2013. The formulations typically comprise an amount of formulation ranging between 20% and 50% w/w relative to the total weight of the formulation, in such a way as to ensure an extract content ranging between 30 and 80 mg per dose, and a proanthocyanidin intake ranging between 9 mg and 25 mg per dose. According to a preferred embodiment, the formulations preferably comprise, in addition to a composition according to the invention, a composition obtainable by the processes described above, and an extract "as is", i.e. not combined with phospholipids.

In a fourth aspect thereof, the invention relates to a method for the prevention or treatment of urinary tract infections, in particular those of the lower urinary tract, which comprises administration of a composition or formulation, preferably a formulation, to a patient requiring it. The method preferably involves administration of an amount of the composition, or preferably the formulation, according to the invention, such as to ensure a daily proanthocyanidin intake ranging between 9 and 25 mg.

The examples below illustrate the invention in greater detail.

Experimental Part

Materials

American cranberry extract (*Vaccinium macrocarpon* Aiton) is commercially available from Indena S.p.A. under the trademark Anthocran®.

Soy lecithin or sunflower lecithin were obtained from Cargill. The maltodextrin used in example 3 was obtained from Roquette. The silicon dioxide used in example 3 was obtained from Grace GmbH & Co. The microcrystalline cellulose used in examples 4 and 5 was obtained from FMC Biopolymer, the magnesium stearate used in examples 4 and 5 was obtained from Peter Greven, the dicalcium phosphate dihydrate used in example 5 was obtained from Budenheim, and the polyvinylpolypyrrolidone used in example 5 was obtained from Ashland.

In examples 1-3, the percentages are percentages by weight relative to the total weight of the composition.

Preparation Examples

Example 1—Composition (C1) Containing American Cranberry Extract and Soy Lecithin

| | |
|---|---|
| American cranberry (*Vaccinium macrocarpon*) extract | 25.0% |
| Soy lecithin | 75.0% |

The composition was obtained by the following process:
1. The extract and the soy lecithin were dispersed in 10 volumes, relative to the total weight of the extract and lecithin, of water-saturated ethyl acetate, under magnetic stirring.
2. The dispersion obtained in step 1 was heated to reflux (about 70° C.) and left in said conditions under stirring for 3 hours.
3. The solvent was removed by low-pressure evaporation from the dispersion obtained in step 2, maintaining the temperature at ≤70° C.
4. Drying of the product obtained in step 3 was completed in a stove under vacuum at 50° C. until an ethyl acetate residue complying with the limits specified in ICH Guideline Q3C (R6) was obtained.
5. The product obtained in step 4 was calibrated on a 60-mesh screen.

Example 2—Composition (C2) Containing American Cranberry Extract and Soy Lecithin

| | |
|---|---|
| American cranberry (*Vaccinium macrocarpon*) extract | 33.3% |
| Soy lecithin | 66.7% |

The composition was obtained by the following process:
1. The soy lecithin was suspended in 15 volumes of technical ethanol under magnetic stirring, heating to 50° C. until a dispersion was obtained.
2. The American cranberry extract was added to the dispersion obtained in step 1 under magnetic stirring. The dispersion was heated to reflux (about 70° C.) and left in said conditions under stirring for 2 hours.
3. The solvent was removed by low-pressure evaporation from the dispersion obtained in step 3, maintaining the temperature at ≤70° C.
4. Drying of the product obtained in step 3 was completed in a stove under vacuum at 50° C. until a solvent residue complying with the limits specified in ICH Guideline Q3C (R6) was obtained.
5. The product obtained in step 4 was calibrated on a 20-mesh screen.

Example 3—Composition (C3) Containing American Cranberry Extract, Sunflower Lecithin, Maltodextrin and Silicon Dioxide

| | |
|---|---|
| American cranberry (*Vaccinium macrocarpon*) extract | 30.0% |
| Sunflower lecithin | 55.0% |
| Maltodextrin | 13.0% |
| Silicon dioxide | 2.0% |

The composition was obtained by the following process:
1. The extract was dispersed in 10 volumes of water-saturated ethyl acetate under magnetic stirring.
2. Lecithin was added under magnetic stirring to the dispersion obtained in step 1.
3. The dispersion was heated to reflux (about 70° C.) and left in said conditions under stirring for 2 hours.
4. Maltodextrin was added to the dispersion obtained in step 3, maintaining the same stirring and temperature conditions as described in step 3 for 30 minutes.
5. The solvent was removed by low-pressure evaporation from the dispersion obtained in step 4, maintaining the temperature at ≤70° C.

6. Drying of the product obtained in step 5 was completed in a stove under vacuum at 50° C. until a solvent residue complying with the limits specified in ICH Guideline Q3C (R6) was obtained.
7. The product obtained in step 6 was calibrated on a 20-mesh screen.
8. Silicon dioxide was added to the product obtained in step 7, in an amount equal to 2% of the mixture, mixing for about 2 minutes in a V-mixer (MultiGel).

Example 4—Formulation (F1) in the Form of Hard Capsules Containing Composition (C1)

| | |
|---|---|
| Composition (C1) | 120.0 mg |
| Microcrystalline cellulose | 133.5 mg |
| Silicon dioxide | 4.5 mg |
| Magnesium stearate | 2.0 mg |

Formulation (F1) was obtained by the following process:
1. Composition (C1) was mixed for about 5 minutes in a V mixer (MultiGel) with microcrystalline cellulose.
2. Silicon dioxide was added to the mixture obtained in step 1, and mixing was continued for about 2 minutes.
3. Magnesium stearate was added to the mixture obtained in step 2, and mixing was continued for about 1 minute.
4. The mixture obtained in step 3 was divided between hard gelatin or plant-based capsules, at the rate of 260 mg/capsule.

Example 5—Formulation (F2) in the Form of Tablets Containing Composition (C1)

| | |
|---|---|
| Composition (C1) | 120.0 mg |
| Dicalcium phosphate dihydrate | 180.0 mg |
| Microcrystalline cellulose | 150.0 mg |
| Polyvinylpolypyrrolidone | 30.0 mg |
| Magnesium stearate | 10.0 mg |
| Colloidal silicon dioxide | 10.0 mg |

Formulation (F1) was obtained by the following process:
1. Composition (C1) was mixed for about 10 minutes in a V mixer (MultiGel) with dicalcium phosphate dihydrate, microcrystalline cellulose and polyvinylpolypyrrolidone.
2. Silicon dioxide was added to the mixture obtained in step 1, and mixing was continued for about 2 minutes.
3. Magnesium stearate was added to the mixture obtained in step 2, and mixing was continued for about 1 minute.
4. The mixture obtained in step 3 was compressed in a rotary tablet press equipped with round concave punch dies having a diameter of 12 mm.

In-Vivo Assays

Example 6—Quantitation in the Urine of the Active Ingredients and Active Metabolites of a Formulation Containing Composition (C1)

The study was performed by administering to healthy volunteers (non-smoking women with a low-polyphenol diet), for one week, two capsules a day, each containing 120 mg of an American cranberry extract not associated with phospholipids, containing 30% proanthocyanidins, amounting to 36 mg of proanthocyanidins [control capsules (F0)].

After a one-week wash-out period, the same volunteers received, again for one week, two capsules of formulation (F1) prepared according to example 4, each containing 120 mg of composition (C1), corresponding to 30 mg of an American cranberry extract containing 30% proanthocyanidins. The urine was collected before the first administration of both the control capsules (F0) and the capsules of formulation (F1), and 1, 2, 4, 6, 10, 12 and 24 hours after the last administration. For the purpose of identification and quantitation in the urine of the analytes associated with the products administered, the urine samples collected were diluted 1:5 v/v with a 1% solution of trichloroacetic acid and then extracted in solid phase on a HyperSep™ C18 column. The extracted metabolites present in the urine were then subjected to acid and enzymatic hydrolysis and subsequently quantified by HPLC-mass spectrometry, using a Zorbax SB-C18 column for the separation and a triple-quadrupole mass spectrometer (TSQ Quantum™ Triple Quadrupole) as detector.

It was surprisingly found that although the amount of American cranberry extract, and therefore of proanthocyanidins, administered with formulation (F1) containing 120 mg of composition (C1) was four times less than the amount administered with the capsules containing the extract "as is" [control capsules (F0)], some metabolites, deriving both from proanthocyanidin and from the other active ingredients of the extract (flavonols and phenolic acids) were more abundant after administration of formulation (F1). In particular, the following metabolites were more abundant, in relation to the amount of extract administered: epicatechin, catechin-3-O-gallate, myricetin-3-β-O-galactoside, myricetin-3-O-glucoside, quercetin-3-O-ramnoside, isorhamnetin-3-O-glucoside, kaempferol-3-O-glucoside, gallic acid, hippuric acid and protocatechuic acid.

Figure 4:
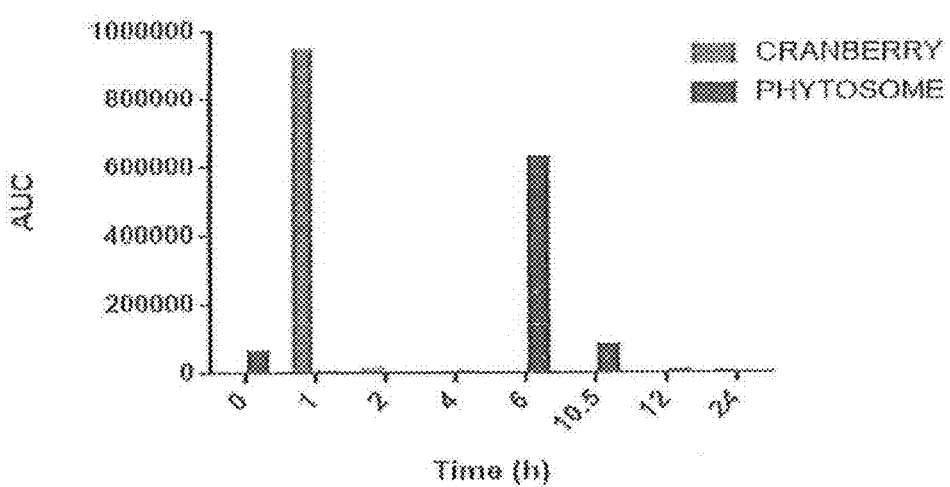
FIG. 4 shows the area under the curve of catechin-3-O-gallate.

The histograms demonstrating this experimental observation are shown in the annexed FIGS. 1-4, which show the area under the curve (AUC) of the four main ingredients of the American cranberry extract: epicatechin (FIG. 1), myricetin-3-O-glucoside (FIG. 2), myricetin-3-β-O-galactoside (FIG. 3) and catechin-3-O-gallate (FIG. 4). The term "CRANBERRY" refers to the data obtained with administration of control capsules (F0), while the term Phytosome refers to the data obtained with administration of the capsules containing composition (C1).

Said data confirm that the composition according to the invention, unlike cranberry extracts not associated with phospholipids, guarantees that measurable, effective levels of the main metabolites of the active ingredients of the extract will be reached in the urine, and therefore in contact with the urothelial mucosa, which represents the substrate of bacterial infections.

It was also surprisingly found that the various metabolites appear in the urine at different times, depending on whether the control formulations (F0) containing the cranberry extract "as is" were administered, or formulations (F1) according to the invention, as clearly shown by the histograms below, wherein the values corresponding to the administration of the control formulations (F0) are captioned "CRANBERRY", while the values corresponding to the administration of formulations (F1) according to the invention are captioned "PHYTOSOME".

This finding demonstrates that by combining an extract "as is" (i.e. not associated with phospholipids) with a composition according to the invention, a long-lasting antibacterial action can be guaranteed in the urothelial mucosa of the lower urinary tract, thus ensuring a more effective preventive action against said recurrent infections.

Example 7—Study of the Efficacy of a Formulation Containing Composition (C1) in Inhibiting Adherence and Biofilm Formation by Various Strains of *Candida albicans*

The efficacy of a formulation containing composition (C1) was assessed in an ex-vivo test, in particular evaluating the cell-adhesion and biofilm-formation inhibition effect on a cell culture inoculated with various strains of *Candida albicans* obtained from vaginal swabs, and from a reference strain of *Candida albicans* (SC5314). The extent of biofilm formation was quantified by staining with gentian violet and subsequent spectrophotometric reading at 540 nm.

Healthy female volunteers were treated for one week with 2 capsules a day, each containing 120 mg of an American cranberry extract not associated with phospholipids, containing 30% proanthocyanidins, amounting to 36 mg of proanthocyanidins [control capsules (F0)]. The cell culture with biofilm was then placed in contact with the urine of said volunteers, and said urine was freeze-dried and reconstituted with the same medium as used for the cell culture (RPMI-1640). After a one-week wash-out period, the same healthy volunteers were treated for one week with two capsules a day of formulation (F1), each containing 120 mg of composition (C1), (corresponding to 30 mg of an American cranberry extract containing 30% proanthocyanidins). In both cases the urine was collected 1, 2, 4, 6, 10, 12 and 24 hours after the last capsule required by the treatment was taken.

The Table 1 below shows the absorbance data relating to the spectrophotometric readings at 540 nm, which quantify the extent of the biofilm present on the cell culture. The values U pre (F0) and U pre (F1) refer to the urine readings before the administrations.

| Composition F(0) | SC5314 | U pre (F0) | (F0) 1 h | (F0) 2 h | (F0) 4 h | (F0) 6 h | (F0) 10 h | (F0) 12 h | (F0) 24 h |
|---|---|---|---|---|---|---|---|---|---|
| MEAN | 1.4272 | 1.3319 | 1.0650 | 1.2624 | 1.3717 | 1.1608 | 1.0467 | 0.8644 | 1.1179 |
| SD | 0.2924 | 0.4094 | 0.3378 | 0.3933 | 0.3261 | 0.4417 | 0.2169 | 0.1253 | 0.1291 |

| Composition F1 | SC5314 | U pre (F1) | (F1) 1 h | (F1) 2 h | (F1) 4 h | (F1) 6 h | (F1) 10 h | (F1) 12 h | (F1) 24 h |
|---|---|---|---|---|---|---|---|---|---|
| MEAN | 1.4272 | 1.2434 | 1.2335 | 0.9742 | 1.2231 | 1.2700 | 1.1579 | 0.8976 | 1.1252 |
| SD | 0.2924 | 0.3659 | 0.2831 | 0.2387 | 0.3507 | 0.4343 | 0.3153 | 0.2507 | 0.2626 |

SC5314 (C+) = biofilm

Comparison of the values demonstrates that the inhibitory activity is clearly manifested in the urine samples collected after 1 and 12 hours in the case of treatment with 120 mg of American cranberry [control capsules (F0)], and in the urine samples collected after 2 and 12 hours in the subjects treated with the capsules of formulation (F1). It was surprisingly found that although formulation (F1) contains an amount of American cranberry extract, and consequently of proanthocyanidins, four times lower than the amount administered with the capsules containing the extract "as is" [control capsules (F0], the inhibitory activity at the times specified above was comparable. It was also surprisingly found that the maximum inhibitory activity took place at different times in the case of administration of the extract of formulation (F0) (1 and 12 hours, P<0.0001, Mann-Whitney test) and formulation (F1) (2 and 12 hours, P<0.0001), demonstrating that by combining an American cranberry extract "as is" (i.e. not associated with phospholipids) with a composition according to the invention, a longer-lasting action inhibiting adhesion and biofilm formation can be guaranteed against the various strains of *Candida albicans*, and therefore a more effective preventive action against recurrent urinary tract infections.

The invention claimed is:

1. A method for treating infections of the lower urinary tract in a patient in need thereof, said method comprising administering to said patient a formulation comprising:

a) 30 to 80 mg of *Vaccinium macrocarpon* extract corresponding to a proanthocyanidin daily intake ranging from 9 mg and 25 mg per dose; and at least one phospholipid in a weight ratio between *Vaccinium macrocarpon* extract and phospholipid ranging between 1:1 and 1:4; and b) 120 mg of *Vaccinium macrocarpon* extract not combined with phospholipids said *Vaccinium macrocarpon* extract containing 30% proanthocyanidins amounting to 36 mg.

2. The method according to claim 1, wherein the composition further comprises one or more technological adjuvants selected from water-soluble or water-insoluble diluents, lubricants and/or glidants and surfactants.

3. The method according to claim 2, wherein the diluent is not a maltodextrin, mannitol, isomalt or a combination thereof.

* * * * *